(12) United States Patent
Mikkonen

(10) Patent No.: US 12,201,553 B2
(45) Date of Patent: Jan. 21, 2025

(54) INSERTER FOR AN INTRAUTERINE SYSTEM

(71) Applicant: Bayer OY, Turku (FI)

(72) Inventor: Joonas Mikkonen, Lempäälä (FI)

(73) Assignee: BAYER OY, Turku (FI)

( * ) Notice: Subject to any disclaimer, the term of this patent is extended or adjusted under 35 U.S.C. 154(b) by 0 days.

(21) Appl. No.: 16/650,796

(22) PCT Filed: Sep. 20, 2018

(86) PCT No.: PCT/EP2018/075477
§ 371 (c)(1),
(2) Date: Mar. 25, 2020

(87) PCT Pub. No.: WO2019/063410
PCT Pub. Date: Apr. 4, 2019

(65) Prior Publication Data
US 2021/0196502 A1    Jul. 1, 2021

(30) Foreign Application Priority Data
Sep. 27, 2017   (EP) ..................................... 17193406

(51) Int. Cl.
*A61F 6/18*     (2006.01)
*A61F 6/14*     (2006.01)

(52) U.S. Cl.
CPC .............. *A61F 6/18* (2013.01); *A61F 6/144* (2013.01)

(58) Field of Classification Search
CPC .. A61K 9/0039; A61B 5/6875; A61B 5/4325; A61B 10/0291; A61B 10/04; A61B 2010/045; A61M 2210/1433; A61M 25/00; A61F 6/08; A61F 6/18; A61F 6/144

USPC .......................................................... 128/840
See application file for complete search history.

(56) References Cited

U.S. PATENT DOCUMENTS

| | | | |
|---|---|---|---|
| 5,000,191 A | 3/1991 | Reiss | |
| 8,479,742 B2 * | 7/2013 | LaPlaca | A61B 17/12159 128/207.14 |
| 2008/0097471 A1 * | 4/2008 | Adams | A61B 17/12136 606/119 |
| 2009/0137970 A1 * | 5/2009 | George | A61B 17/4241 604/271 |
| 2011/0162656 A1 * | 7/2011 | Jutila | A61F 6/144 128/830 |

FOREIGN PATENT DOCUMENTS

| | | | |
|---|---|---|---|
| CN | 204121251 U | 1/2015 | |
| CN | 204581458 U * | 8/2015 | |
| WO | WO2010031900 A1 | 3/2010 | |
| WO | WO-2016125176 A1 * | 8/2016 | A61B 17/320708 |

* cited by examiner

*Primary Examiner* — Ophelia A Hawthorne
*Assistant Examiner* — Michael Milo
(74) *Attorney, Agent, or Firm* — MORRISON & FOERSTER LLP

(57) ABSTRACT

The present invention relates to an inserter for an intrauterine system, comprising a handle (1,11), an insertion tube (4) having a longitudinal direction and connected to the handle, and a plunger (3) arranged inside the insertion tube. The inserter also comprises a force sensor (6, 5 9) arranged between the insertion tube and the handle. The insertion tube is partially arranged inside the force sensor in such a manner that when force is exerted on the insertion tube along its longitudinal direction, the insertion tube is arranged to move with respect to the force sensor.

10 Claims, 3 Drawing Sheets

INSERTER FOR AN INTRAUTERINE SYSTEM

CROSS REFERENCE TO RELATED APPLICATIONS

This application is a National Phase application under 35 U.S.C. § 371 of International Application No. PCT/EP2018/075477, filed Sep. 20, 2018, which claims priority benefit of European Application No. 17193406.0, filed Sep. 27, 2017.

FIELD OF THE DISCLOSURE

The present disclosure relates to an inserter for an intrauterine system, comprising a handle, an insertion tube having a longitudinal direction and connected to the handle, and a plunger arranged inside the insertion tube.

BACKGROUND OF THE DISCLOSURE

Various types of inserters have been developed for the positioning of mechanical and copper wire-containing intrauterine devices (IUDs) as well as of intrauterine systems having a drug containing cylinder (IUSs). In the following, the acronyms IUD and IUS can be used interchangeably and when one is mentioned, it is to be understood that either of them can be used. Simple rod-shaped inserters have been suggested for inserting relatively small or sufficiently flexible intrauterine devices in their original, expanded shape by using simple push-in technique. However, most common inserters are constructed for introducing the device into the uterus in a contracted state. These inserters usually comprise an insertion tube having a relatively narrow diameter and a rounded, blunt end which will pass through the cervical canal easily and will not damage or injure the fundus upon contact therewith, and a plunger inside the insertion tube. Prior to insertion, the device, whether an IUD or an IUS, is usually retracted into the insertion tube either by means of string(s) attached to the device and intended for the removal of the device from the uterus, or by pushing the device into the insertion tube by a plunger with inserters having a special window to adapt the device in the expanded shape. Then the insertion tube with the device therein is introduced through the cervical canal into the uterus. When the device is correctly positioned, it is released either by pushing the plunger towards the uterus or by holding the plunger steady and by retracting the insertion tube outwards. Once expulsed from the insertion tube within the uterine cavity, the device is supposed to resume its original expanded shape.

During insertion, perforation of the uterine wall by the intrauterine system is a potentially serious problem that can occur in approximately one every 1000 to 2500 insertions. Perforation can happen if the insertion pressure is more than the perforation resistance of the uterine fundus. In currently used inserters, the person carrying out the insertion can only rely on his/her hand and feeling to evaluate the insertion force.

SUMMARY OF THE DISCLOSURE

There exists thus a need to provide a means for preventing perforation of uterine wall during insertion of an IUS. There exists also a need to provide means for measuring the insertion force, that would be easy and reliable for use. An aim is thus also to increase patient security and easiness of use for the physician.

The present description relates to an inserter for an intrauterine system, comprising a handle, an insertion tube having a longitudinal direction and connected to the handle, and a plunger arranged inside the insertion tube. The inserter further comprises a force sensor arranged between the insertion tube and the handle, and that the insertion tube is partially arranged inside the force sensor in such a manner that when force is exerted on the insertion tube along its longitudinal direction, the insertion tube is arranged to move with respect to the force sensor.

The present description also relates to an arrangement comprising an inserter as herein described and an intrauterine system.

DETAILED DESCRIPTION

Figure 1:
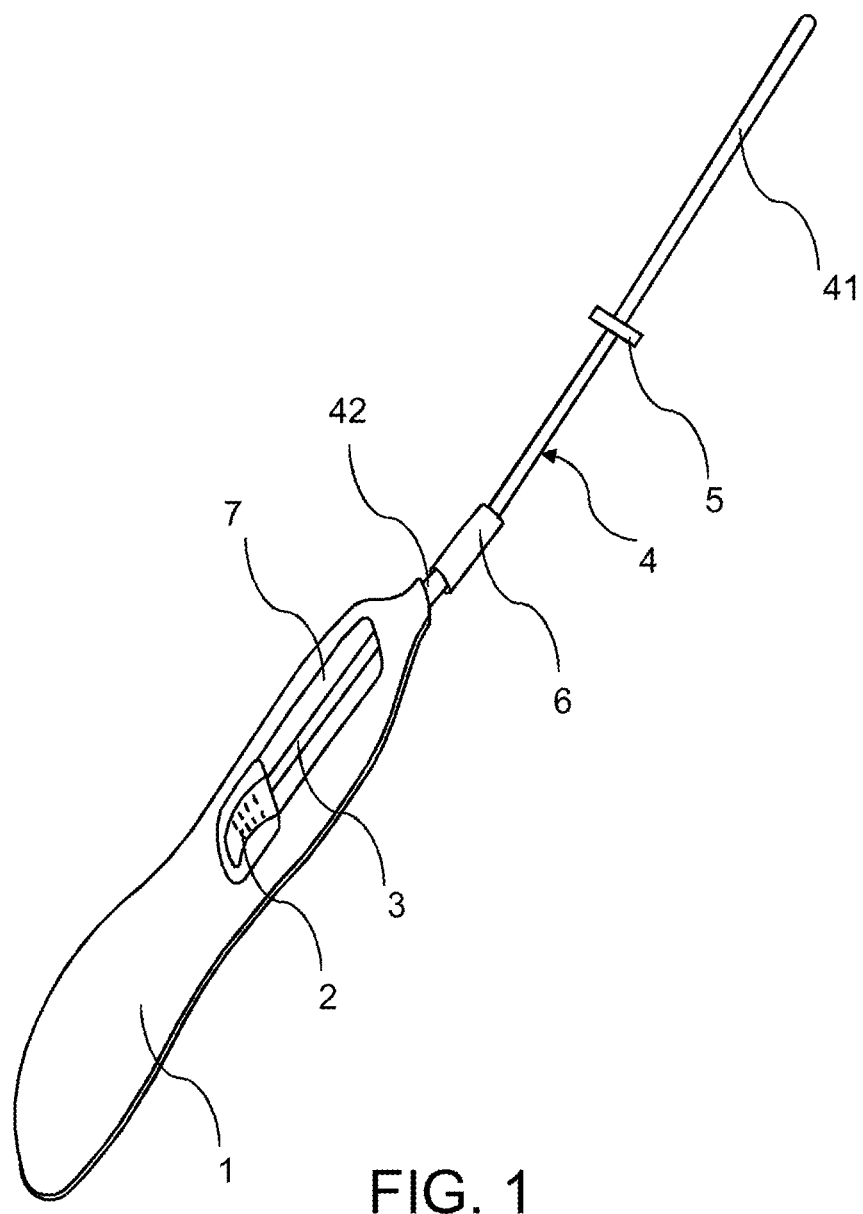
FIG. 1 schematically illustrates an inserter according to an embodiment.

The present description relates to an inserter for an intrauterine system, comprising a handle, an insertion tube having a longitudinal direction and connected to the handle, and a plunger arranged inside the insertion tube. The inserter further comprises a force sensor arranged between the insertion tube and the handle, and that the insertion tube is partially arranged inside the force sensor in such a manner that when force is exerted on the insertion tube along its longitudinal direction, the insertion tube is arranged to move with respect to the force sensor.

Embodiments of the present invention relate to an inserter for an intrauterine system comprising a force sensor. The force sensor is arranged between the insertion tube and the handle in such a manner that when force is exerted on the insertion tube during insertion, the movement of the force sensor makes the stress exerted on the insertion tube visible to the user. Thus the user will have a clear, visual indication on the amount of force exerted on the insertion tube, and to evaluate the risk of perforating uterine wall.

The force sensor typically has a linear force-compression curve. The range of insertion force as well as the typical perforation force has been described in literature. Thus the normal force for insertion is in the area of 0-10 N, while a force in the area of 10-20 N is typically still below perforation force. In some embodiments, the insertion tube is equipped with visual indicators arranged to be visible depending on a position of the force sensor. For example, a first visual indicator (for example a green line) can be visible while the force used is below 10 N. When the force exceeds 10 N, a second visual indicator (for example an orange line) becomes visible, and the user of the inserter can thus see that he or she should take care and monitor the insertion process.

Further, if the force exceeds 20 N, a third visual indicator (for example a red line) becomes visible. At this point, the user knowns that cervix should be dilated again, and insertion started again from the beginning.

In some embodiments, the insertion tube comprises at least two visual indicators arranged to be visible depending on a position of the force sensor. There can be two, three, four, five, six or more visual indicators on the insertion tube. The visual indicators can be identical or different. The visual indicators can be for example lines of different colours, such as green and orange or green, orange and red. Alternatively, the visual indicators can be numbers, such as 1 and 2; 1, 2 and 3; or 1, 2, 3 and 4. In some embodiments, the visual indicators are equally spaced lines or lines of different thicknesses. The visual indicators are typically arranged close to the force sensor and on that part of the insertion tube that moves with respect to the force sensor.

The visual indicators can be arranged to become visible or to become invisible, depending on their location on the insertion tube.

The movement of the force sensor is typically rather small, for example in the order of 2-5 mm in the longitudinal direction. The longitudinal direction of the force sensor is the same as the longitudinal direction of the insertion tube and in fact of the whole inserter.

The inserter in whole in indeed typically a longitudinal object, i.e. its length is its largest dimension. Each part of the inserter thus has a first end and a second end, and a longitudinal direction that extends between these ends.

In the present description and claims, by first ends are typically meant the ends that are closer to the uterus during the insertion of the intrauterine system, also called forward ends. Second ends are the ends opposite to the first ends, also called distal ends. The term removal string means one or more strings used for removing the intrauterine system once it reaches the end of its use time. There may thus be one or more such strings, and this term encompasses also strings that are not used for removal but only for locking the device during insertion.

The force sensor typically has an outer shell and an inner member designed to contract when force is exerted on the insertion tube along its longitudinal direction.

In some embodiments, the force sensor comprises a spring arranged to contract when force is exerted on the insertion tube along its longitudinal direction. In some embodiments, the force sensor comprises another means arranged to contract or shorten, when force, i.e. pressure, is exerted on it. For example, the force sensor may comprise a piece made of a compressible material such as rubber or another compressible elastomer. It may also comprise an airtight module filled with air. In some embodiments, the force sensor comprises an inner member having a wedge-shape, and the inner surface of the outer shell is designed accordingly, such that the forms block together at a certain point. A still other possibility is that the inner member is attached to the inner wall of the shell by one or more pins, which will break or give away when sufficient force is exerted on the force sensor.

The handle can have many shapes and is preferably designed for easy handling of the inserter even by using only one hand. The plunger is advantageously hollow or has a groove or bore running in the axial direction thus allowing the string(s) to slide freely in it, without any risk of them getting jammed between the plunger and the insertion tube. The first end, i.e. the forward end of the plunger is preferably suitably shaped to have for example a notch, an indentation, an eyelet, a funnel or a groove to adapt to the lower end of the intrauterine system and to enable optimal and secure positioning of the intrauterine system on the plunger so that the probability of damage to the intrauterine system is minimal. Thus, the IUS will not be twisted when it is drawn in the insertion tube or during insertion and assumes a specified constant configuration when released.

Additionally, the insertion tube may comprise a flange, which can be adjusted so that its distance from the first end of the insertion tube corresponds to the depth of the uterus.

The force sensor can be attached directly to the handle, but it can also be arranged between two parts of the insertion tube, while in this case still being between the handle and the insertion tube, as such.

Thus, in some embodiments, the insertion tube comprises a first part and a second part, the second part is connected with the handle, the force sensor is arranged between the first part and the second part, and the first part is partially arranged inside the force sensor and the second part is attached to the force sensor.

In some embodiments, the insertion tube comprises a first part and a second part, the second part is connected with the handle, the force sensor is arranged between the first part and the second part, and the second part is partially arranged inside the force sensor and the first part is attached to the force sensor.

Thus, in case the insertion tube is divided into two parts, one of the parts of the insertion tube is attached on the force sensor in a fixed manner, while the other part is attached to the force sensor in a movable manner. Preferably, it is the part of the insertion tube that is closer to the handle that is attached to the force sensor in a movable manner, while the distal part is attached to the force sensor in a fixed manner. This enables the user to better visualise the movement of the force sensor with respect to the handle, as the gap between the force sensor and the distal tip of the handle gets smaller. In some embodiments, visual indicators can also be dispensed with, as the size of the gap is easy to follow.

The present description thus relates also to an inserter for an intrauterine system, comprising a handle having a first end and a second end, an insertion tube, and a plunger having a first end and a second end, and arranged inside the insertion tube. The inserter further comprises a force sensor comprising a first end and a second end, wherein the insertion tube comprises a first part having a first end and a second end, and a second part having a first end and a second end, the first end of the first part of the insertion tube is arranged inside the second end of the force sensor and the second end of the first part of the insertion tube is connected with the first end of the handle, the second end of the second part of the insertion tube is attached to the first end of the force sensor, and the force sensor comprises a spring arranged between the first end of the first part of the insertion tube and the first end of the force sensor.

The present force sensor can be used in connection with different types of inserters. In some embodiments, the handle of the inserter comprises a longitudinal opening and the inserter comprises means for withdrawing the intrauterine system inside the insertion tube, said means comprising a movable slider arranged in said longitudinal opening.

In some embodiments, the plunger is movably arranged inside the insertion tube and the insertion tube is attached to a first end of the handle. Alternatively, the plunger is attached to the handle, and the insertion tube is attached to the slider.

In some embodiments, the inserter is as follows:
the handle of the inserter has a longitudinal opening at its first end, said opening having a longitudinal axis parallel to the longitudinal axis of the inserter,
the first handling means comprises
a movable slider arranged in said longitudinal opening and having a first end and a second end, and
locking means for reversibly locking the intrauterine system in relation to the plunger,
the second handling means is a plunger having a first end and a second end, attached by its second end to the slider,
the insertion tube is arranged around the plunger, and the inserter further comprises locking means for reversibly locking the intrauterine system in relation to the plunger via a removal string of the intrauterine system.

One type of inserter especially suitable for use in the present arrangement is as described in WO 2010/031900, the contents of which are hereby incorporated by reference. In this embodiment, the insertion tube is in two parts even in the case the force sensor is attached directly to the first end of the handle, as it continues inside the handle, too.

In some embodiments, one inserter that is particularly suitable for the present description comprises a handle, a plunger attached to the handle, a slider, an insertion tube around the plunger, the second end of the insertion tube being attached to the slider or to the means to move the slider. The inserter also comprises means for reversibly locking the removal string(s) of the intrauterine system in such a way that the IUS remains immobile in relation to the plunger during the necessary steps prior to and during insertion, and again for releasing the string(s) and the IUS after it has been inserted. The inserter further comprises an opening in a part of the handle and a channel in which the insertion tube slides in the longitudinal direction. The longitudinal opening on the handle can be also quite narrow and does not need to be symmetrically positioned on the handle and with respect to the longitudinal axis.

The part of the handle that is closer to its first end has an opening having a first end and a second end, which opening runs in the direction of the plunger. The surface of the first end of the slider and the surface at the first end of the opening together form a first pair of stop members, and the surface of the second end of the slider and the surface at the second end of the opening together form a second pair of stop members. When inserting the IUS, the slider and the insertion tube can be moved forward until the surfaces and contact each other, and backwards until the surfaces and contact each other. The locking means are arranged inside the handle.

The slider mechanism, when used, is preferably inside the handle and comprises at least one elongated element, which can be moved in the longitudinal direction of the plunger. According to an embodiment the slider comprises means to move the slider, which preferably is a part of the slider, and the insertion tube attached to said means. In some embodiments, the slider comprises at least two elements, preferably parallel, which are combined on at least one point by a transversal member. The transversal member may form means, for example a knob or switch, by which the slider can be moved. The handle can comprise one or more means to connect the slider elements and to facilitate the movement of the slider, for example a support, a shoulder, a holder, a saddle, a groove or a slot. The slider preferably comprises at least one structural element, for example an extension, which is capable to generate the necessary operation of the locking means to keep the strings immobilized during storage or during preparatory steps before insertion or during insertion and/or to release the string(s) when the slider is moved to the backward position. In this description, the term slider is used to designate both the slider itself and the means to move the slider attached to the slider. The term slider is thus used for convenience of reading.

In some embodiments, the inserter further comprises locking means for reversibly locking the intrauterine system via a removal string of the intrauterine system. Depending on the type of the inserter, the locking means may be controllable by the slider or by the first part of the insertion tube.

The locking means is any arrangement which, induced by the movement of the slider or of the means to move the slider and the insertion tube, can immobilise the removal string(s) to hold the IUS in a stable position and/or to release the string(s) after insertion to release the IUS. The locking means can be for example according to what has been described in WO 2010/031900. Particularly, the locking means comprises an object capable of reversibly preventing and/or allowing the movement of the string(s) by at least partly moving or pivoting from the original position, for example rotating around a shaft or an axle, and vertically or horizontally attached to the handle. The object may have several shapes and may be for example round or rod-shaped, wedge, polygonal or rectangular with rounded or sharp corners. The surface of the object preferably comprises one or more extensions having variable size and shape, for example a knob, a rib or a switch. When the slider mechanism is moving backwards, at a suitable point a part or an extension of the slider or of the insertion tube is pressed against at least one extension of the object thus changing its orientation enough relative to the original position to cause release of the string(s). Preferably the object has a slot or pinhole through which the string(s) run. The locking means may also comprise at least one counterpart against which the string(s) are pressed by the object and thus reversibly immobilized in the locking position. The counterpart has a suitable shape adapted to fit at least some part of the surface of the object. An extension, or extensions of the object can be used to keep the object and the counterpart in a fixed configuration until the slider is moved backwards to release the IUS. The counterpart preferably has a suitable design to keep the string(s) in proper direction, for example a slot or pinhole through which the string(s) run. Further, the object and said at least one counterpart have preferably a suitable length and diameter to fit inside the handle.

The present description also relates to an arrangement comprising an inserter as herein described and an intrauterine system. The various embodiments and features listed above thus apply mutatis mutandis to the present arrangement. In some embodiments, the intrauterine system of the arrangement comprises a T-shaped body and an elastomeric capsule containing a therapeutically active agent. The inserter is however not limited to T-shaped IUS's, but can be used for any kind of IUS's, for example having a 7-shaped or rounded body.

Indeed, a typical example of an intrauterine device has a T-shaped body fabricated of plastic material and consisting of an elongated body part having at one end a transverse member comprising two wings, the elongate member and the transverse member forming a substantially T-shaped piece when the device is in the expanded configuration, for example positioned in the uterus. The tips of these wings are preferably hemispherical in order to facilitate the introduction of the device through the cervical canal. The elongate member has a copper spiral or wire or a hormone capsule arranged around the body. The end of the vertical body part has a loop with a string or strings attached to it, with which the device can be removed from the uterus after use or whenever needed.

In some embodiments, the intrauterine system comprises a triangular shaped body and at least one capsule containing a therapeutically active agent. The intrauterine systems may also comprise more than one capsule, and each capsule may comprise a different therapeutically active agent. One capsule may also comprise more than on therapeutically active agent. The therapeutically active agents are any agents known and useful as such, for example contraceptives or agents benefiting from a local release in the uterus.

The inserter is introduced into the uterus until the IUS is in the correct location (this can be for example be shown with the help of the flange as mentioned above), where after the device is released from the insertion tube. Depending on the inserter type, either the plunger is pushed forward to push the IUS out of the insertion tube, or the insertion tube is retracted towards the handle by moving the slider backwards until the distal surface of the slider abuts the distal surface of the opening (at its second end) of the handle. The distance the plunger or the slider and the insertion tube can be moved has been selected to indicate clearly the moment at which the IUS has completely been released from the insertion tube.

In the following description, the term slider and the corresponding reference number are used to designate both the slider itself and the means to move the slider attached to the slider. The term slider is thus used for convenience of reading.

FIG. 1 schematically illustrates an inserter according to some embodiments. The inserter comprises a handle 1, a slider 2, a plunger 3 and an insertion tube 4 around the plunger. A flange 5 has been arranged on the insertion tube, as well as a force sensor 6. In some embodiments, the insertion tube 4 is in two parts, a first part 41 and a second part 42, arranged on both sides of the force sensor 6. The inserter further comprises an opening 8 in a part of the handle.

Figure 2:
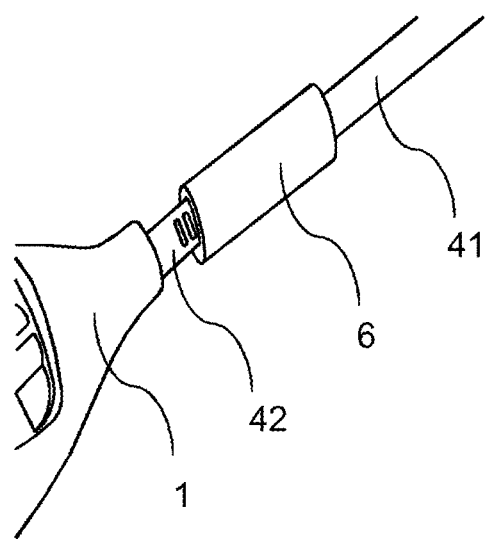
FIG. 2 is an enlargement of a part of FIG. 1.

FIG. 2 is an enlargement of a part of FIG. 1. The Figure shows the first end of the handle 1, the second part 42 of the insertion tube, the force sensor 6 and the first part of the insertion tube 41.

Figure 3:
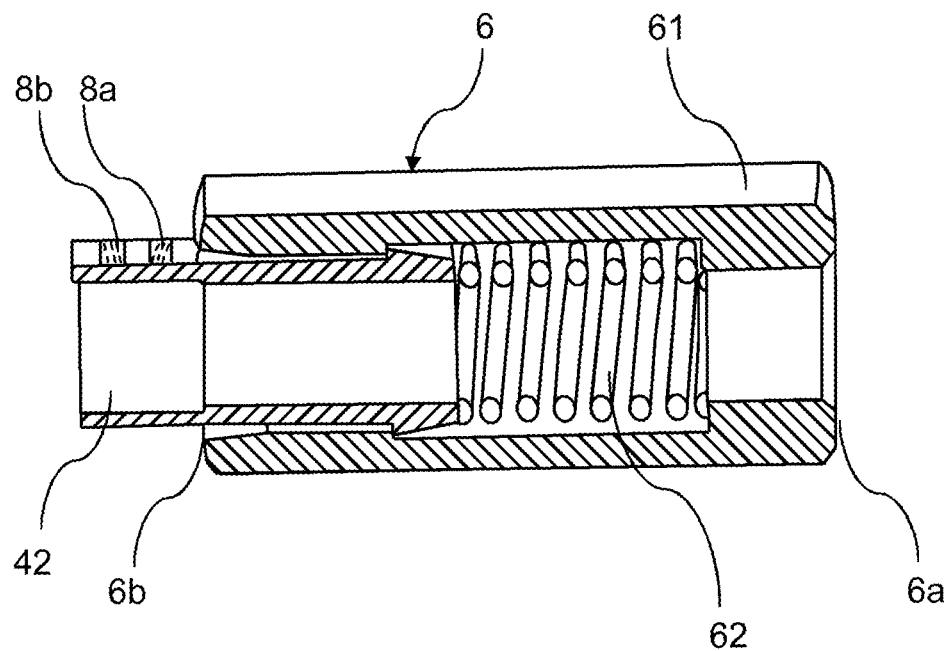
FIG. 3 is a partial cross-sectional view of FIG. 1.

FIG. 3 is a partial cross-sectional view of FIG. 1. It illustrates the outer shell 61 of the force sensor 6 and its inner member, which is a spring 62 in this embodiment. The second part 42 of the insertion tube is arranged in connection with the force sensor 6, and partially inside it, at the second end 6b of the force sensor. The size of the spring 62 is such that when the first end 6a of the force sensor is under pressure by the first part of the insertion tube (not shown but fixedly attached to the first end 6a of the insertion tube), it compresses and then pushes the force sensor 6 towards the handle (from right to left in the Figure), thus making the first visual indicator 8a invisible and only the second visual indicator 8b visible.

Figure 4:
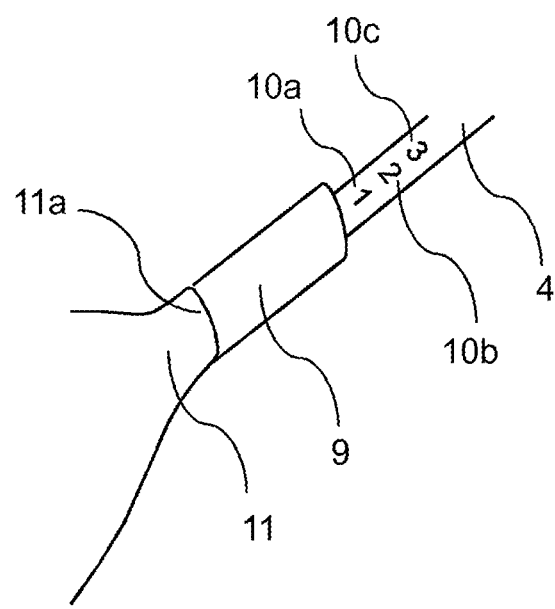
FIG. 4 is a partial illustration of an inserter according to another embodiment.

FIG. 4 is a partial illustration of an inserter according to some embodiments. Force sensor 9 is attached directly to the first end 11a of the handle 11, and the insertion tube 4 is in one part. There are three visual indicators 10a, 10b and 10c arranged on the insertion tube 4.

The invention claimed is:

1. An inserter for an intrauterine system, comprising: a handle; an insertion tube having a longitudinal direction, wherein the insertion tube comprises a first part and a second part and the second part is connected to the handle; a plunger arranged inside the insertion tube; a force sensor comprising an outer shell and a spring arranged between the first part and the second part, wherein the first part of the insertion tube is fixedly attached to the force sensor and the second part of the insertion tube is movably attached to the force sensor; and a visual indicator, wherein the first part of the insertion tube is partially arranged inside the outer shell in such a manner that when force from inserting the intrauterine system is exerted on the first part of the insertion tube along its longitudinal direction, the second part of the insertion tube is arranged to longitudinally and distally move against the spring to contract the spring, and the visual indicator is configured to indicate to a user when the insertion tube moves with respect to the force sensor, and when the intrauterine system is released, the second part of the insertion tube is arranged to longitudinally and proximally move to return the spring to a less contracted state.

2. The inserter of claim 1, comprising a locking means for reversibly locking the intrauterine system via a removal string of the intrauterine system, wherein the locking means comprises an extension configured to change orientation when engaged by one of the slider or insertion tube.

3. The inserter of claim 2, wherein the locking means is controllable by the slider.

4. The inserter of claim 2, wherein the locking means is controllable by the insertion tube.

5. An arrangement comprising the inserter of claim 1, and the intrauterine system.

6. The arrangement of claim 5, wherein the intrauterine system comprises a T-shaped body and an elastomeric capsule containing a therapeutically active agent.

7. The inserter of claim 1, wherein the insertion tube comprises at least two visual indicators arranged to be visible depending on a position of the force sensor.

8. The inserter of claim 1, wherein the handle comprises a longitudinal opening and the inserter comprises means for withdrawing the intrauterine system inside the insertion tube, comprising a movable slider arranged in said longitudinal opening.

9. The inserter of claim 1, wherein the plunger is movably arranged inside the insertion tube and the insertion tube is attached to a first end of the handle.

10. The inserter of claim 1, wherein the plunger is attached to the handle, and the insertion tube is attached to the slider.

* * * * *